Figure 4:
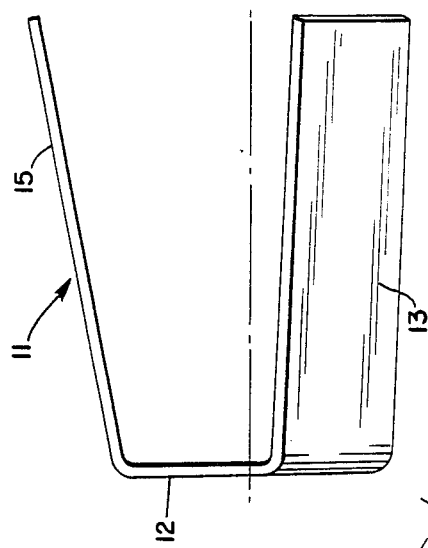

United States Patent [19]

Jörnéus et al.

[11] Patent Number: 4,763,788

[45] Date of Patent: Aug. 16, 1988

[54] STERILE PACKAGE

[76] Inventors: Lars Jörnéus, Björkväktarens gata 27, S-415 16 Göteborg; Bo Rangert, Klarbärsvägen 1, S-435 00 Mölnlycke, both of Sweden

[21] Appl. No.: 939,738

[22] Filed: Dec. 9, 1986

[30] Foreign Application Priority Data

Dec. 12, 1985 [SE] Sweden .................................. 8505866

[51] Int. Cl.$^4$ ...................... A61B 17/06; A61B 19/02; B65D 53/00; B65D 81/00
[52] U.S. Cl. .................................. 206/438; 206/524.8
[58] Field of Search ............................ 206/438, 524.8

[56] References Cited

U.S. PATENT DOCUMENTS 2,479,581  8/1949  Masci .................................. 206/438

Primary Examiner—William Price

[57] ABSTRACT

The invention relates to a package for sterile and contamination free storage and transport of artificial implants (2), comprising a hermetically sealed outer casing (3) preferably made of glass, and an inner capsule to hold the implant, made of the same material as the implant (2) itself. The inner capsule comprises an open sleeve (1) preferably tubular, closed at one end by the implant (2) itself, so that the part (2a) of the implant which is intended for tissue integration is sealed by the sleeve (1).

7 Claims, 2 Drawing Sheets

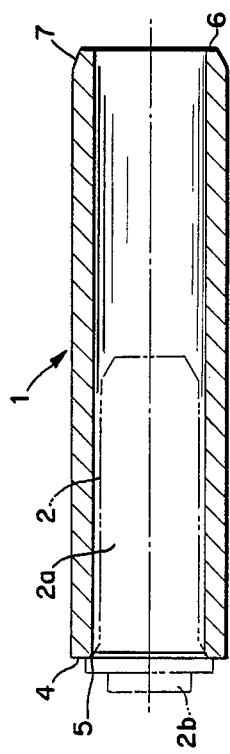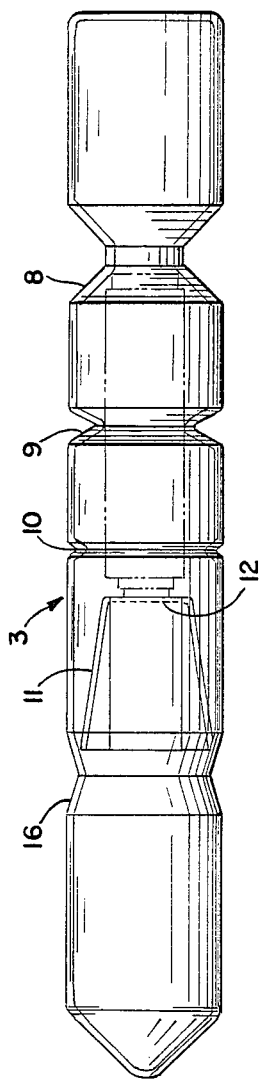

U.S. Patent  Aug. 16, 1988  Sheet 2 of 2  4,763,788

STERILE PACKAGE

The present invention relates to a package for sterile and contamination free storage and transport of artificial implants, comprising a hermetically sealed outer casing, preferably of glass, and an inner capsule to hold the implant, made of the same material as the implant.

Such a package, which can be generally used for all types of artificial implants, instruments, etc., which can withstand sterilization temperatures, is previously known by Swedish patent application No. 8406592-9.

Said package is principally intented to be used for titanium fixtures which are used to provide attachment means for artificial teeth, dental bridges, prosthesis parts, etc. Such titanium fixtures have a high degree of biocompability which is intimately associated with the surface layer of the fixture. The surface layer must be carefully controlled and specified at atom level. The known package guarantees that the surface layer remains unaltered from manufacture to use so that the implantation process is not jeopardized.

The known inner capsule comprises a cylindrical body with a screw-on lid preferably made of titanium. The titanium capsule protects the titanium fixture within the capsule against mechanical damage and ensures that the titanium fixture comes into direct contact only with titanium.

The known inner capsule has some disadvantages however. Two separate, threaded parts, the cylindrical body and the screw-on lid, means a comparatively high manufacturing cost and the deep recess in the cylindrical body also means a high manufacturing cost as well as cleaning difficulties.

Said design also means a comparatively high weight of the inner capsule relative to the implant, which means strength property problems for an outer casing made of glass in case of shocks during transport.

The object of the present invention is to provide a package which fulfils the demands for sterility and guarantees freedom from contamination down to the atom level but which also reduces the manufacturing costs as well as the weight of the inner capsule.

Said known package also has certain drawbacks with respect to the handling of the package. When the outer glass casing is broken, the inner capsule cannot be reached but must be emptied out. This means that the inner capsule must have a firm lid to prevent the implant from falling out and become contaminated. This handling of the inner capsule and its opening are disturbing extra moment during the operation.

A further object of the invention is therefore to provide a package which is so designed that the handling of it at the operation is facilitated. The inner capsule is also so designed that it can easily be placed in an operation stand.

The invention is mainly characterized in that the inner capsule comprises an open sleeve, preferably tubular, closed at one end by the implant itself, so that the part of the implant, which is intended for tissue integration, is sealed by the sleeve.

By making the inner capsule in the form of a thin tubular member the manufacturing of the package is substantially simplified and the cleaning is also facilitated. The inner capsule protects the implant from coming into contact with glass like the previously known package. That the inner capsule is sealed by the implant itself means that the part of the implant intended for tissue integration is protected against undesired gas contact directly from the closed sealed end of the capsule and by forming the contact of the glass casing with the inner capsule as a seal the undesired gas is prevented from passing the inner capsule at the closure.

Said sealings can not be made absolutely gas tight but they prevent transport of warm gas, which means that gases with high condensation temperature, such as $B_2O_3$, at the closure are condensated on the walls and do not reach the implant.

According to a further, suitable embodiment the inner capsule is fixed in its position by means of a simple spring, which at the same time is a first bar against penetration of undesired gases to the inner capsule.

Figure 3:
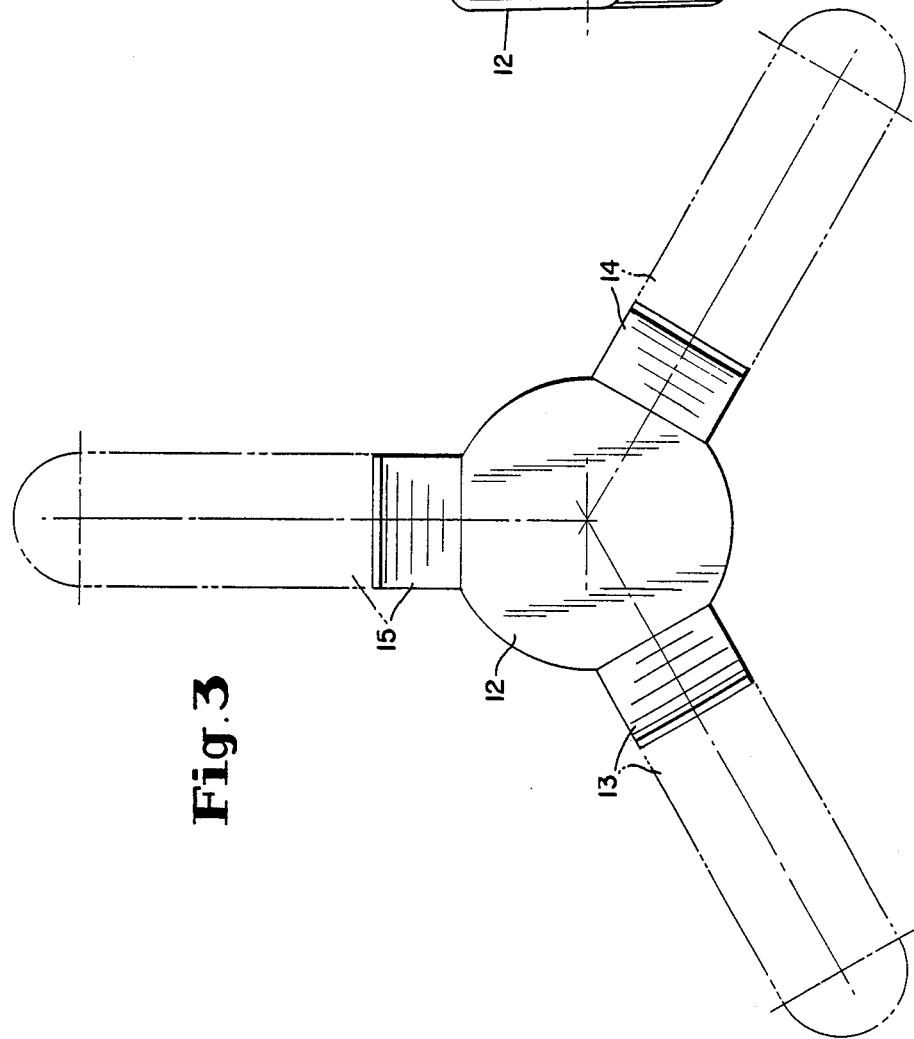

In the following the invention will be described in more detail with reference to the accompanying drawings in which FIG. 1 shows a view of the inner capsule in the form of a tubular sleeve, FIG. 2 shows a view of the outer casing in the form of a glass ampoule and FIG. 3 shows the positioning member in the form of a simple spring.

The inner capsule shown in FIG. 1 consists of an open tubular sleeve 1 preferably made of titanium. The sleeve 1 is designed to hold a titanium fixture 2, the position of which is indicated by dashed lines in the Figure. The titanium sleeve 1 provides protection against mechanical damage and has the advantage, like the previously known package, that the titanium fixture 2 only comes into direct contact with titanium. Like the previously enclosed titanium package the titanium sleeve is neither sterile nor absolutely gas-tight per se and does not therefore protect the surface of the titanium fixture from all types of impurities. The titanium sleeve is therefore positioned in a glass ampoule 3 (outer casing), see FIG. 2, which both maintains the sterility and protects the surface of the titanium fixture inside the titanium sleeve from impurities.

One end 4, the closure end, of the tubular titanium sleeve 1 is adapted to the outer diameter of the titanium fixture so that the fixture 2 can be pushed into the titanium sleeve from the closure end into a position in which a conical outer surface of the titanium fixture is in contact with a corresponding conical surface of the end 4 of the titanium sleeve so that the titanium sleeve is closed by the titanium fixture itself. In this way the part 2a of the titanium fixture which is intended for tissue integration is protected from undesired contact of gases directly from the closed end. Only the parts 2b of the titanium fixture which do not come into direct contact with the tissue are positioned "open" in the titanium sleeve.

The other end 6 of the titanium sleeve has rounded corners 7 and provides a sealing by its contact with the glass ampoule. In this way also the other end of the titanium sleeve is sealed.

The titanium sleeve is centered in the glass ampoule 3 by means of impressions in the wall of the ampoule, a large impression or stud 8 near the end of the glass ampoule against which stud the end 6 of the titanium sleeve is in contact, as well as a central impression 9 abutting the cylindrical surface of the titanium sleeve providing a support also for the closed end part of the titanium sleeve. Also this last-mentioned impression can be designed as a sealing between the glass ampoule and the titanium sleeve preventing undesired gases to pass.

The glass ampoule 3 is provided with a fractural impression 10 for opening the ampoule so located on the glass ampoule that the titanium sleeve can be easily taken and removed from the ampoule. The removal is also facilitated by the fact that the sleeve is centered within the outer casing by means of the impression 9. The axial protruding part of the titanium sleeve after the glass ampoule has been broken and the radial play between the inner and outer casings have been chosen so that the broken removed part of the outer casing does not come into contact with the inner capsule when broken, which otherwise could give rise to an uncontrolled fracture of the outer casing.

The breaking of the glass ampoule is also facilitated by the sealing impression 9 centering the titanium sleeve.

The titanium sleeve 1 is secured in its position by means of a spring 11 providing a first bar against penetration of undesired gases to the inner capsule. The spring is provided with a circular, plane part 12 and three legs 13, 14, 15 abutting a conical stud 16 of the inner surface of the glass ampoule by spring force. The plane part 12 of the spring is in contact with the end part of the titanium fixture and is pressing the fixture against the conical surface 5 in the inner capsule. After the outer casing has been broken the spring is separated from the inner capsule as the inner capsule and the spring then are located in different parts of the divided outer casing. The spring is also preferably made of titanium to prevent contamination.

The invention is not limited to the illustrated embodiment but can be varied within the scope of the following claims.

We claim:

1. A package for sterile and contamination-free storage and transport of artificial implants, comprising a hermetically sealed glass outer casing and an inner capsule to hold the implant made of the same material as the implant itself, characterized in that the immer capsule comprises an open sleeve closed at one end by the implant itself so that the part of the implant which is intended for tissue integration is sealed by the sleeve, the outer surface of the sleeve forms a seal by contact with the outer casing so that the other end of the sleeve is also closed, and having spring means for urging the sleeve into a defined position in the outer casing.

2. A package according to claim 1 characterized in that the spring means provides a bar against penetration of undesired gases through the closed end of the sleeve.

3. A package according to claim 1 characterized in that the sleeve has a conical inner surface against which the implant is pressed by the spring means.

4. A package according to claim 1 characterized in that the outer casing has a central impression which centers the sleeve inside the outer casing.

5. A package according to claim 4 characterized in that a seal is formed at the contact of the central impression and the outer surface of the sleeve.

6. A package according to claim 1 characterized in that the outer casing is provided with a fractural impression so located that the sleeve protrudes in the axial direction sufficient to be easily taken out by an instrument after the outer casing has been broken away.

7. A package according to claim 6 characterized in that there is sufficient difference between the outer casing diameter and the sleeve diameter that when the outer casing has been broken away, the separated part of the outer casing does not come into contact with the sleeve.

* * * * *